US011241578B2

(12) United States Patent
Naitoh

(10) Patent No.: US 11,241,578 B2
(45) Date of Patent: Feb. 8, 2022

(54) URINARY INCONTINENCE TREATMENT DEVICE

(71) Applicant: KYOTO PREFECTURAL PUBLIC UNIVERSITY CORPORATION, Kyoto (JP)

(72) Inventor: Yasuyuki Naitoh, Kyoto (JP)

(73) Assignee: KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 196 days.

(21) Appl. No.: 16/484,291

(22) PCT Filed: Feb. 9, 2018

(86) PCT No.: PCT/JP2018/004732
§ 371 (c)(1),
(2) Date: Aug. 7, 2019

(87) PCT Pub. No.: WO2018/147447
PCT Pub. Date: Aug. 16, 2018

(65) Prior Publication Data
US 2020/0001080 A1    Jan. 2, 2020

(30) Foreign Application Priority Data
Feb. 13, 2017   (JP) .............................. JP2017-023817

(51) Int. Cl.
*A61N 1/36* (2006.01)
*A61F 13/42* (2006.01)
(Continued)

(52) U.S. Cl.
CPC .......... *A61N 1/36007* (2013.01); *A61F 13/42* (2013.01); *A61N 1/0484* (2013.01);
(Continued)

(58) Field of Classification Search
CPC ............ A61N 1/36007; A61N 1/36031; A61N 1/36034
(Continued)

(56) References Cited

U.S. PATENT DOCUMENTS

| 3,678,928 A | 7/1972 | Mozes |
| 2013/0013022 A1 | 1/2013 | De Oliveira Barroso Junior |

(Continued)

FOREIGN PATENT DOCUMENTS

| CN | 103860334 A | 6/2014 |
| GB | 680088 A | 10/1952 |

(Continued)

OTHER PUBLICATIONS

International Search Report dated May 1, 2018 from International Application No. PCT/JP2018/004732, 4 pages, including English translation.

(Continued)

*Primary Examiner* — Amanda K Hulbert
*Assistant Examiner* — Philip C Edwards
(74) *Attorney, Agent, or Firm* — MH2 Technology Law Group, LLP

(57) ABSTRACT

The present invention provides a nocturnal enuresis treatment device 1 including a sensor 10 for detecting urination; one or more stimulation pads 20 constituted to impart a stimulus to a wearer; and a mechanical portion 30 including the following: (i) a stimulus generation unit 31 for generating a signal for causing the stimulation pads 20 to impart the stimulus to the wearer, and (ii) a control unit 32 for generating a signal for causing the stimulus generation unit 31 to generate the stimulus in response to urination detection by the sensor.

6 Claims, 6 Drawing Sheets

(51) Int. Cl.
*A61N 1/04* (2006.01)
*A61F 13/84* (2006.01)
(52) U.S. Cl.
CPC ....... *A61N 1/0492* (2013.01); *A61N 1/36031* (2017.08); *A61N 1/36034* (2017.08); *A61F 2013/424* (2013.01); *A61F 2013/425* (2013.01); *A61F 2013/8482* (2013.01)
(58) Field of Classification Search
USPC .......................................................... 607/41
See application file for complete search history.

(56)        References Cited

U.S. PATENT DOCUMENTS

| 2014/0303682 | A1* | 10/2014 | Siff | A61N 1/36034 |
| | | | | 607/41 |
| 2015/0352357 | A1* | 12/2015 | Wei | A61N 1/36031 |
| | | | | 604/385.03 |
| 2016/0136420 | A1 | 5/2016 | Brink et al. | |
| 2017/0203100 | A1* | 7/2017 | Imran | A61N 1/36007 |

FOREIGN PATENT DOCUMENTS

| JP | S49-019599 B1 | 5/1974 |
| JP | 2002-200178 A | 7/2007 |
| WO | 2015/160676 A1 | 10/2015 |

OTHER PUBLICATIONS

National Hospital Organization Kanazawa Medical Center, "Low Frequency Therapy to Urinary Incontinence (UroMaster, NODOKA)", National Hospital Organization Kanazawa Medical Center Leaflet, Nov. 6, 2015, 5 pages with English translation.

Pharmaceuticals and Medical Devices Agency, "Uromaster (interference low frequency therapeutic apparatus for urinary frequency and urinary incontinence)", Attachment of medical instruments, Pharmaceuticals and Medical Devices Agency, Jul. 10, 2012, 5 pages with partial English translation.

Odagaki et al., "Efficiency of Electrical and Magnetic Stimulation for Treatment of Urinary Incontinence*—Using Computer Model of Female Abdomen", Transactions of The Japanese Society for Medical and Biological Engineering, Japan Society of Medical Electronics and Biological Engineering, Sep. 10, 2003, vol. 41, No. 3, , pp. 213-220 with English abstract.

Oredsson et al., "Changes in Nocturnal Bladder Capacity During Treatment With the Bell and Pad for Monosymptomatic Nocturnal Enuresis", The Journal of Urology, 1998, vol. 160, pp. 166-169.

Hvistendahl et al., "The Effect of Alarm Treatment On the Functional Bladder Capacity in Children With Monosymptomatic Nocturnal Enuresis", The Journal of Urology, 2004, vol. 171, pp. 2611-2614.

Kawauchi et al., "Enuresis alarm treatment". Nocturnal Enuresis Study, 2009, vol. 14, pp. 65-69, with English abstract.

Nakanishi et al., "Interferential low—frequency wave therapy for enuresis and incontinence with small functional bladder capacity", Nocturnal Enuresis Study, 2004, vol. 9, pp. 67-71, with English abstract.

Nakagawa et al, "Effects of the sacral surface therapeutic electrical stimulation for refractory enuresos", Nocturnal Enuresis Study, 2009, vol. 14, pp. 71-75 with English abstract.

* cited by examiner

URINARY INCONTINENCE TREATMENT DEVICE

CROSS-REFERENCE TO RELATED APPLICATIONS

This application is a U.S. National Stage application of PCT/JP2018/004732 filed 9 Feb. 2018, which claims priority to Japanese Application No. 2017-023817 filed 13 Feb. 2017, the entire disclosures of which are incorporated herein by reference.

TECHNICAL FIELD

The present invention mainly relates to a urinary incontinence treatment device.

BACKGROUND ART

Urinary incontinence refers to involuntary urination and pathologically poses social and hygienic problems. Urinary incontinence has a considerable effect on the quality of life (QOL) of patients, as well as on their close family members (e.g., parents and caretakers).

One of the pathological conditions of urinary incontinence is nocturnal enuresis. Typical treatments for nocturnal enuresis include drug therapy and alarm therapy recommended by the International Children's Continence Society and the Japanese Society on Enuresis (Non-patent literature (NPL) 1, NPL 2, and NPL 3). These therapies are performed widely, not only in Japan, but also in the world. FIG. 1 shows an outline of alarm therapy.

In alarm therapy, an alarm sound is emitted when a sensor detects urination, and in response to the sound, the mother wakes the patient up. Repetition of this operation (alarm treatment) is said to increase nocturnal bladder capacity, leading to a cure of nocturnal enuresis.

During urination (nocturnal enuresis) while continuing to sleep, the patient is stimulated by hearing this sound and being woken up by the mother, which is believed to gradually increase bladder capacity. That is, the alarm treatment aims to increase bladder capacity to make the storage of urine possible until morning, rather than make it possible to be woken up at night.

NPL 3 discloses that alarm therapy is expected to achieve a 130% increase in nocturnal bladder capacity within a month.

However, alarm treatment is problematic since it cannot be carried out without the cooperation of family members, such as the mother, and family members must agree to an alarm sound throughout the house at night. In fact, in clinical sites, alarm treatment is given up on due to the mother becoming stressed and tired or due to refusal by the patients themselves or their families.

Known therapeutic means to treat nocturnal enuresis or urinary incontinence also include electrical stimulation treatment (e.g., low-frequency treatment) (NPL 4, NPL 5, and Patent Literature (PTL) 1). FIG. 2 shows an outline of electrical stimulation therapy.

NPL 5 discloses that low-frequency treatment for 30 days achieved an increase of about 150% in nocturnal bladder capacity.

PTL 1 discloses a pelvis surface stimulation electrode instrument and an undergarment for wearing the pelvis surface stimulation electrode instrument. PTL 1 discloses enhancing pelvic floor muscle group strength by appropriately stimulating, with stimulation waves, the skin right above the second to fourth posterior sacral foramina at the both back sides of sacrum and/or motor points on the pudendal nerve skin inside the tuber ischiadicum of the buttocks so as to neuromodulate the urine nerve mechanism, treat urination disorders, and prevent degradation of pelvic floor muscle groups to increase muscle tension. However, PTL 1 nowhere mentions imparting a stimulus at a specific time.

Regarding drug therapy, therapeutic effects have been confirmed with administration of desmopressin, which is an antidiuretic hormone drug, administration of an anticholinergic drug, administration of a tricyclic antidepressant, etc. However, drug therapy often cannot be applied to a patient due to side effects.

For example, administration of an anticholinergic drug, which is also effective for daytime urinary incontinence, is known to cause side effects, such as dry throat, constipation, and progression of dementia.

Since these treatments are not easy, and since their therapeutic effects are not sufficient, the development of a novel method for treating nocturnal enuresis is in demand at present. The development of a novel method for treating urinary incontinence other than nocturnal enuresis is also in demand.

CITATION LIST

Patent Literature

PTL 1: JP2002-200178A

Non-Patent Literature

NPL 1: Oredsson, A. F. and Jorgensen, T. M. J Urol.; 160: 166-9, 1998
NPL 2: Hvistendahl GM. J Urol.; 171: 2611-4, 2004
NPL 3: Akihiro KAWAUCHI et al.; Nocturnal Enuresis Study, 14: 65-69, 2009
NPL 4: Kimihiro NAKANISHI et al., Nocturnal Enuresis Study, 9: 67-71, 2004.
NPL 5: Haruo NAKAGAWA et al., Nocturnal Enuresis Study, 14: 71-75, 2009

SUMMARY OF INVENTION

Technical Problem

A main object of the present invention is to provide a urinary incontinence treatment device.

One of the specific objects is to provide a nocturnal enuresis treatment device as a means for achieving the effect of alarm treatment, i.e., an increase in bladder capacity, without deteriorating the quality of life (QOL) of patients with nocturnal enuresis themselves and their families (e.g., mothers).

Solution to Problem

To achieve the above object, the present inventor conducted extensive research to search for a method to achieve the fundamental object of the alarm treatment, i.e., an increase in bladder capacity, even without the cooperation of the mother or family, by imparting a stimulus to a patient with nocturnal enuresis (a child) immediately upon the occurrence of nocturnal enuresis in the child.

The present inventor focused on electrical stimulation treatment (e.g., low-frequency treatment), which is known as one of the treatment methods for nocturnal enuresis. FIG. 2 shows an outline of electrical stimulation therapy.

DOCUMENTS

Kimihiro NAKANISHI et al., Interferential low-frequency wave therapy for enuresis and incontinence with small functional bladder capacity: Nocturnal Enuresis Study 9, 67-71, 2004

Haruo NAKAGAWA et al., Effects of the sacral surface therapeutic electrical stimulation for refractory enuresis: Nocturnal Enuresis Study 14, 71-75, 2009

Electrical stimulation treatment has been reported to promote an increase in bladder capacity, leading to a cure of nocturnal enuresis. Its mechanism of action is believed to mainly lie in that stimulation onto afferent pathways in the sacral spinal cord region suppresses detrusor contraction and increases bladder capacity. Electrical stimulation treatment is performed either in a medical examination room or at home by using a compact device that is brought into the house. In either case, the treatment is usually performed about twice a day at specific time periods. Of electrical stimulation treatments, low-frequency treatment does not cause any pain and is minimally invasive to patients. However, electrical stimulation treatment is not prioritized as a therapeutic means since its therapeutic effect on nocturnal enuresis is not sufficiently satisfactory.

Under such circumstances, the present inventor has conceived of a method for imparting stimulus with low frequency to the bladder instead of imparting stimulus by sound and by the mother in the alarm treatment.

The present inventor has also found that this method can be used for treating urinary incontinence other than nocturnal enuresis.

Based on these findings, the present inventor conducted further research. The present invention has thus been accomplished.

The present invention encompasses the following embodiments.

Item 1. A urinary incontinence treatment device including:
a sensor for detecting urination;
one or more stimulation pads configured to impart a stimulus to a wearer; and
a mechanical member including the following:
(i) a stimulus generation unit for generating a signal for causing the stimulation pads to impart the stimulus to the wearer, and
(ii) a control unit for causing the stimulus generation unit to generate the signal in response to urination detection by the sensor.

Item 2. The device according to Item 1, wherein the sensor, the stimulation pads, and the mechanical member are attachable to a diaper.

Item 3. The device according to Item 2, further including a diaper, wherein the sensor, the stimulation pads, and the mechanical member are attached to the diaper.

Item 4. A urinary incontinence treatment device, which is attachable to a diaper with a sensor for detecting urination, the device including:
one or more stimulation pads configured to impart a stimulus to a wearer, and
a mechanical member including the following:
(i) a stimulus generation unit for generating a signal for causing the stimulation pads to impart the stimulus to the wearer,
(ii) a sensor element connecting part for connecting the sensor to the mechanical member, and
(iii) a control unit connected to the sensor element connecting part and for causing the stimulus generation unit to generate the signal in response to urination detection by the sensor.

Item 5. A urinary incontinence treatment device, which is attachable to a diaper with a sensor for detecting urination and one or more stimulation pads configured to impart a stimulus to a wearer,
the device including a mechanical member including the following:
(i) a stimulus generation unit for generating a signal for causing the stimulation pads to impart the stimulus to the wearer,
(ii) a sensor element connecting part for connecting the sensor to the mechanical member, and
(iii) a control unit connected to the sensor element connecting part and for causing the stimulus generation unit to generate the signal in response to urination detection by the sensor.

Item 6. The device according to any one of Items 1 to 5, wherein the stimulation pads are configured to be adhered to the skin over the sacrum at the back.

Item 7. The device according to any one of Items 1 to 6, wherein the mechanical member is configured to be positioned at the abdomen.

Item 8. The device according to any one of Items 1 to 7, further including a waterproof member for protecting the stimulation pads from the urination.

Item 9. The device according to any one of Items 1 to 8, wherein the stimulus generation unit supplies an electrical signal to the stimulation pads, and wherein the stimulation pads are electrode pads configured to impart an electrical stimulus to the wearer in response to the supply of the electrical signal.

Item 10. The device according to Item 9, wherein the electrical signal has a frequency of 10 to 50 Hz, and the electrode pads have an output current of 5 to 30 mA and an output voltage of 5 to 60 V.

Item 11. The device according to any one of Items 1 to 10, which is for children.

Item 12. The device according to any one of Items 1 to 10, which is for adults.

Item 13. A method for treating urinary incontinence, the method comprising:
detecting the presence or absence of urination by a sensor; and
imparting a stimulus to a wearer by one or more stimulation pads in response to urination detection by the sensor.

Advantageous Effects of Invention

The present invention provides a novel urinary incontinence treatment device.

According to a preferable embodiment of the present invention, the treatment device is applied to a patient with nocturnal enuresis, and immediately after urination, a switch for electrical stimulus, such as low-frequency waves, is set to on to impart a stimulus for suppressing the detrusor contraction while the patient continues to sleep.

A combination of the alarm treatment and electrical stimulation treatment exerts synergistic effects. More specifically, from the standpoint of the alarm treatment, an effect that is more excellent than the effect of conventional alarm treatment is expected by directly stimulating the nerves involved in suppressing contraction of bladder detrusor muscles, rather than indirectly stimulating the patient with sound aurally or by the mother waking the patient up.

From the standpoint of electrical stimulation treatment, the combination is expected to achieve results that are more excellent than the effect of conventional electrical stimulation treatment by stimulating the nerves involved in suppressing detrusor contraction at the very moment when the detrusor is contracting, rather than simply imparting a stimulus of low-frequency waves at any time period of a day.

In particular, as demonstrated in the Examples, the combination in the treatment of nocturnal enuresis exerted a significantly greater therapeutic effect with a short-time treatment than the alarm treatment or electrical stimulation treatment alone. Further, the combination can more greatly alleviate the burden on both the patients themselves and on their close family members than can conventional methods.

Accordingly, the present invention is expected to exert a high therapeutic effect, as well as improve the QOL of both the patients themselves and their close family members who nurse or care for the patient.

DESCRIPTION OF EMBODIMENTS

Urinary Incontinence

Figure 1:
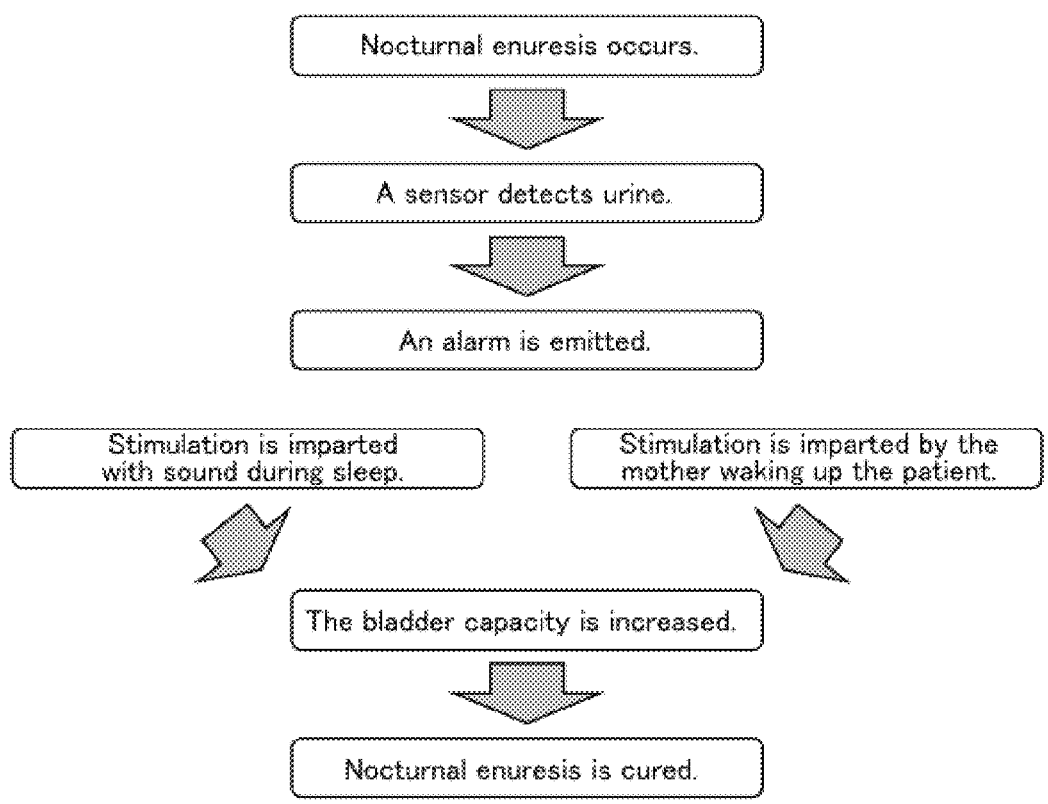
FIG. 1 is a flow chart of an outline of the mechanism of conventional alarm treatment.
Figure 2:
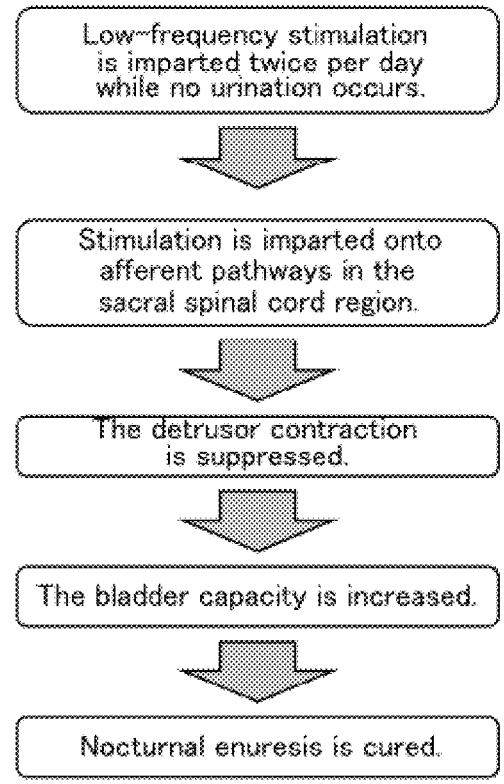
FIG. 2 is a flow chart of an outline of the mechanism of conventional low-frequency treatment.

A disease to be treated by the device of the present invention is urinary incontinence. In particular, the device exerts a preferable therapeutic effect on urinary incontinence caused by insufficient bladder capacity.

Examples of pathological conditions of urinary incontinence include nocturnal enuresis. Among diseases related to urinary incontinence (enuresis), nocturnal enuresis refers to urine leakage that occurs only during sleep (in particular, urine leakage that occurs during sleep at night). More specifically, nocturnal enuresis is distinguished from urinary incontinence (daytime urinary incontinence) in which urine leakage occurs only while awake (daytime) or from enuresis (urinary incontinence) in which urine leakage occurs both during daytime and at night.

Nocturnal enuresis can be categorized into primary nocturnal enuresis in which the patient has never been dry, and secondary nocturnal enuresis in which the patient has previously been dry for at least 6 months. In general, children at the age of 5 or older can be diagnosed with nocturnal enuresis, and children at the age of around 7 or older (after entrance into elementary school) can be treated.

The treatment methods for nocturnal enuresis include lifestyle guidance, behavior therapy, and pharmacotherapy. Of these, alarm treatment as a behavior therapy, and administration of drugs, such as a tricyclic antidepressant and an antidiuretic hormone drug, are known to stably exert effective effects. If necessary (for example, if a single therapy is not successful for a patient), these treatment methods may be used in combination.

Urinary incontinence can be categorized into (1) stress urinary incontinence, (2) urge urinary incontinence, (3) overflow urinary incontinence, and (4) functional urinary incontinence. In this case, (1) stress urinary incontinence and (2) urge urinary incontinence also serve as preferred treatment targets of the present invention. Stress urinary incontinence refers to leakage of urine upon abdominal pressure while urine is stored. Urge urinary incontinence refers to the sudden need to urinate while urine is stored, resulting in involuntary leakage.

Patients with central nervous system diseases, such as cerebrovascular disorder, Parkinson's disease, multiple system atrophy, brain tumor, and dementia, can suffer from urinary incontinence. Further, spinal cord diseases, such as spinal cord injury, multiple sclerosis, spinal cord tumor, spinal cord degenerative disease, and spinal cord vascular disorder, can be accompanied by urinary incontinence. Urinary incontinence due to urine storage disorders in patients with central nervous system diseases or patients with spinal cord diseases also serves as a treatment target of the present invention.

The term "treatment" as used herein refers to, for example, control of urine leakage during sleep when the treatment is for nocturnal enuresis, and the term encompasses inhibition of urine leakage and reduction in the frequency of urine leakage.

Device

Figure 3:
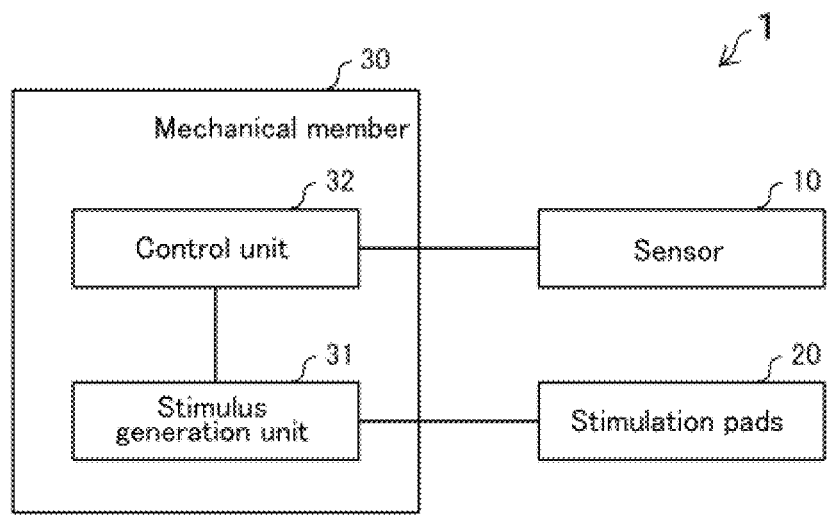
FIG. 3 is an example of an embodiment of the present invention.

As shown in FIG. 3, a urinary incontinence treatment device 1 according to one embodiment of the present invention basically includes the following structure.

A sensor 10 for detecting urination;

one or more stimulation pads 20 configured to impart a stimulus to a wearer; and a mechanical member 30 including the following:
(i) a stimulus generation unit 31 for generating a signal for causing the stimulation pads 20 to impart the stimulus to the wearer, and
(ii) a control unit 32 for causing the stimulus generation unit 31 to generate the signal in response to urination detection by the sensor 10.

Sensor

The sensor 10 of the device 1 according to one embodiment of the present invention is not particularly limited as long as the sensor can detect urination. The sensor 10 monitors wetness conditions based on electrical characteristics (physical property values), such as resistance values, impedance, and capacitance, that change according to wetness conditions. Based on the change in electrical characteristics, the sensor 10 detects leakage, thereby detecting urination. Specific examples include a sensor with a sensor element comprising one pair of conductors (disposed apart from each other), and a detection circuit electrically connected to each of the conductors.

The sensor 10 can detect urination based on the difference between the electrical characteristics in the presence of urine (water) and the electrical characteristics in the absence of urine (water) at the detection area of the sensor (e.g., the area between the pair of conductors). Since urine (water) is conductive, such a difference in the electrical characteristics is created.

For example, for detecting urination in view of an electrical resistance value, the electrical resistance value is relatively high in a dry state in which no urine (water) is present, and the electrical resistance value decreases when it becomes wet due to urination. For detecting urination in view of conductance, the conductance is relatively low in a dry state in which no urine (water) is present, and the conductance increases when it becomes wet due to urination.

In one embodiment of the invention, the sensor element is separable and electrically connected to the sensor connection site. The separable sensor element may be provided with the diaper described later.

In a preferred embodiment of the device according to the present invention, the sensor element of the sensor 10 is positioned at or near the urination part.

Stimulus

Examples of stimulus imparted to a wearer by the urinary incontinence treatment device 1 according to one embodiment of the present invention include electrical stimulus (e.g., low-frequency stimulus and high-frequency stimulus), magnetic stimulus, and thermal stimulus (e.g., warm-temperature stimulus and low sensation stimulus).

From the viewpoint of exerting a high therapeutic effect of urinary incontinence treatment, an electrical stimulus and magnetic stimulus are preferred, and an electrical stimulus is particularly preferred.

Stimulation Pad

The stimulation pads 20 of the device 1 according to one embodiment of the present invention are configured to impart a stimulus to the wearer.

In a preferred embodiment of the present invention (when the stimulus is an electrical stimulus), the stimulation pads 20 are electrode pads. The electrode pads are configured to give an electrical stimulus to the wearer. The electrode pads have a structure according to an electrode pad that is used in a known electrical treatment device for low-frequency treatment etc. In the electrode pads according to one embodiment of the present invention, an electrode element and a gel portion to be adhered to the surface of the body are integrated. The gel portion is preferably made of a material having adhesiveness and conductivity (e.g., a water-containing urethane gel and a water-containing acrylic gel).

The electrode pads, which are electrically connected to the mechanical member 30 described later through a lead wire or the like, receive an electrical signal from the mechanical member 30, and supply the electrical signal to the body portion to which the electrode pads are adhered.

The electrode pads are provided as a pair. The number of pairs may be one or more, and is preferably one or two.

The electrode pads are preferably positioned so as to be able to stimulate the nerve groups that control the bladder. Specifically, for example, one pair of the electrode pads may be positioned at the lower part of the abdomen or at the lower part of the buttocks; or two pairs in total of the electrode pads may be positioned at the lower part of the abdomen (one pair) and the lower part of the buttocks (the other pair). In particular, the electrode pads are preferably positioned on the skin immediately above the sacrum in the lower part of the abdomen. At this site, the afferent pathways in the sacral spinal cord region, which controls urination from bladder, are located.

When the stimulus is a magnetic stimulus, the stimulation pads 20 are magnetic stimulation pads configured to give a magnetic stimulus to the wearer. For example, the magnetic stimulation pads can include a coil in which an electric wire is annularly wound and that can produce a magnetic field when the current flows. The magnetic stimulation pads can have a structure according to a stimulation pad used in a known magnetic treatment device.

When the stimulus is a thermal stimulus, the stimulation pads 20 are thermal stimulation pads configured to give a thermal stimulus to the wearer. For example, for a warm-temperature stimulus, the thermal stimulation pads can have a known heater element.

In a preferred embodiment of the device 1 of the present invention, the stimulation pads 20 are configured to be positioned on the skin over the sacrum at the back.

Mechanical Member

The mechanical member 30 includes a stimulus generation unit 31 for generating a signal for causing the stimulation pads 20 to impart a stimulus to the wearer; and a control unit 32 for causing the stimulus generation unit 31 to generate a stimulus in response to urination detection by the sensor. The main function of the mechanical member 30 is to generate a stimulus when the sensor 10 detects urination, so as to cause the stimulation pads 20 to impart a stimulus to the wearer. The stimulus generation unit 31 and the control unit 32 can be accomplished in a hardware manner, such as by using a logic circuit formed on an integrated circuit (IC) chip. Alternatively, the stimulus generation unit 31 and the control unit 32 can be accomplished in a software manner. In this case, the mechanical member 30 includes a CPU for executing program instructions, memory for the CPU to run the program, auxiliary storage for storing the program and various data, and the like. When the CPU executes the program, the stimulus generation unit 31 and the control unit 32 are accomplished.

In a preferred embodiment of the device 1 of the present invention, the mechanical member 30 is configured to be positioned at the abdomen to achieve a higher effect.

Stimulus Generation Unit

In a preferred embodiment of the present invention (when the stimulus is an electrical stimulus), the stimulus generation unit 31 is an electrical signal generation unit. The electrical signal generation unit generates an electrical signal (AC voltage signal and AC current signal) of a predetermined frequency using a power source as a source of electrical power, based on the control of the control unit 32, and supplies the signal to the electrode element of the electrode pads.

The frequency can be appropriately set by those skilled in the art as long as the object of the present invention is not impaired. For example, the frequency can be about 0.1 to 5000 Hz, preferably about 1 to 500 Hz, more preferably about 5 to 100 Hz, and particularly preferably about 10 to 50 Hz. For example, the frequency may be set in advance or may be input via a frequency input means that may be included in the control unit 32 described later. From the viewpoint of simplifying the device 1, the frequency is preferably set in advance.

The output current and the output voltage can be appropriately set by those skilled in the art as long as the object of the present invention is not impaired. For example, the output current may be about 1 to 100 mA, preferably about 1 to 50 mA, and more preferably about 5 to 30 mA. The output voltage may be about 1 to 100 V, preferably about 2 to 80 V, and more preferably about 5 to 60 V. From the viewpoint of simplifying the device 1, the output current and the output voltage are preferably set in advance.

Setting the frequency, the output current, and the output voltage as described above enables an appropriate stimulus to be given to the wearer without waking the wearer up.

In one embodiment of the present invention, the electrical signal generation unit has a structure according to an electrical signal generating means of a known electrical treatment device for use in low-frequency treatment etc.

Examples of such a known electrical treatment device include the NODOKA low-frequency treatment device produced by Lintec Corporation, Uromaster produced by Medical Taskforce, Co., Ltd., and the like.

When the stimulus is a magnetic stimulus or a thermal stimulus, the stimulation generation unit (signal generation unit) 31 supplies a signal (e.g., current) for causing the stimulation pads 20 to generate a stimulus, based on the control of the control unit 32. When the stimulus is a magnetic stimulus, a specific example of the stimulus generation unit 31 has a structure according to a magnetic generating means of a known magnetic treatment device. Examples of such a known magnetic treatment device include the Uromaster and NicoWave produced by Medical Taskforce, Co., Ltd.

Control Unit

The control unit 32, which is electrically connected to the sensor 10 and the stimulus generation unit 31, causes the stimulus generation unit 31 to generate a signal for causing the stimulus pads 20 to impart a stimulus to the wearer in response to urination detection by the sensor 10.

For example, in a preferred embodiment of the present invention (when the stimulus is an electrical stimulus), the control unit 32 is electrically connected to the sensor 10 and an electrical signal generation unit (the stimulus generation unit 31), and causes the electrical signal generation unit to generate an electrical signal in response to urination detection by the sensor 10. More specifically, when the sensor 10 detects urination (wet state) equal to or more than a predetermined threshold value, the control unit 32 sends a control signal to the electrical signal generation unit so as to cause the electrical signal generation unit to generate an electric signal for a predetermined duration of time.

The time for generating the electrical signal can be appropriately set by those skilled in the art as long as the object of the present invention is not impaired. For example, the time for generating the electrical signal may be about 10 seconds to 30 minutes, preferably about 5 to 20 minutes, and particularly preferably about 15 minutes. For example, the time for generating the electrical signal may be set in advance or may be input via a time input means described later that can be included in the control unit 32. From the viewpoint of simplifying the device 1, the time for generating the electric signal is preferably set in advance.

The control unit 32 can further include the following means:

a frequency input means for inputting a frequency of the electrical signal (making it possible to set a frequency for an individual patient);

a time input means for inputting a time for generating the electrical signal (making it possible to set a frequency for an individual patient);

a switch for forcibly sending a control signal to the electrical signal generation unit to cause the electrical signal generation unit to generate an electrical signal, regardless of the detection by the sensor (forced generation switch);

a switch for forcibly stopping to send a control signal for generating an electrical signal, regardless of the detection by the sensor (forced stop switch).

When the stimulus is a magnetic stimulus or a thermal stimulus, the control unit 32 can have a structure as described above.

Diaper

In a preferred embodiment of the present invention, the sensor 10, the stimulation pads 20, and the mechanical member 30 are attachable to a diaper. In addition to a diaper, they are also attachable to undergarments worn at the crotch.

Figure 4:
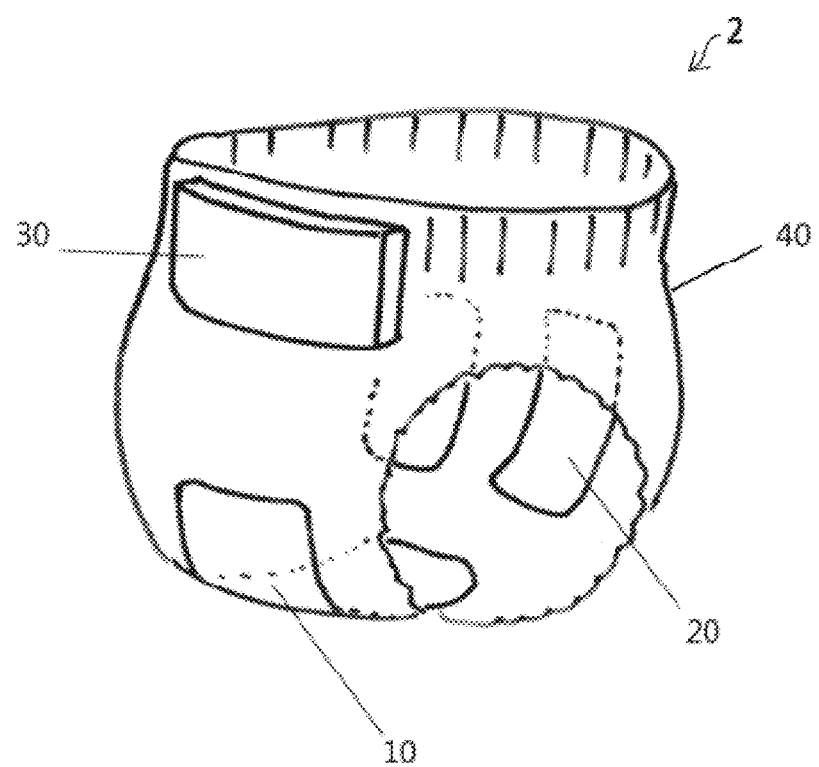
FIG. 4 is an example of an embodiment of the present invention.

FIG. 4 shows an embodiment in which the sensor 10, the stimulation pads 20, and the mechanical member 30 are attached to a diaper 40. This embodiment serves as a urinary incontinence treatment device 2, which is also encompassed by the present invention. In this case, the urinary incontinence treatment device 2 can also be referred to as an "incontinence treatment diaper."

The term "diaper" refers to an absorbent article worn at the crotch of a wearer to absorb and retain liquids, such as urine. The diaper 40 is usually disposable.

The structure of the diaper 40 is known. It is usually composed of exterior body parts that serve as a front body part and a back body part when worn, and an absorbent material for crosslinking the front body part and the back body part. When the diaper 40 is worn, the water-absorbent body is located at the crotch of a wearer to absorb and retain liquids, such as urine excreted from the wearer. The water-absorbent body comprises a water-absorbing material, such as a superabsorbent polymer.

The diaper 40 may be for children (including infants, toddlers, and school children, in particular, grade school children (about 6 to 12 years old)), or may be for adults.

When the diaper 40 is for children, the urinary incontinence treatment device of the present invention is suitably used to treat pediatric patients with nocturnal enuresis. In use of the urinary incontinence treatment device of the present invention, it is not necessary for the mother etc. to wake the patient up, which greatly reduces the burden on both the mother and the patient, as compared with conventional alarm therapy.

When the diaper 40 is for adults, the urinary incontinence treatment device of the present invention is suitably used to treat patients with urinary incontinence (including daytime urinary incontinence), particularly elderly patients. Treatment with the use of the urinary incontinence treatment device of the present invention can reduce the frequency of urinary incontinence to allow the patient to avoid or reduce the need to wear a diaper. This makes it possible, for example, to prevent the patient's motivation from decreasing and dementia from progressing. Furthermore, the reduction in the frequency of urinary incontinence greatly reduces the burden on the caretaker.

Figure 5:
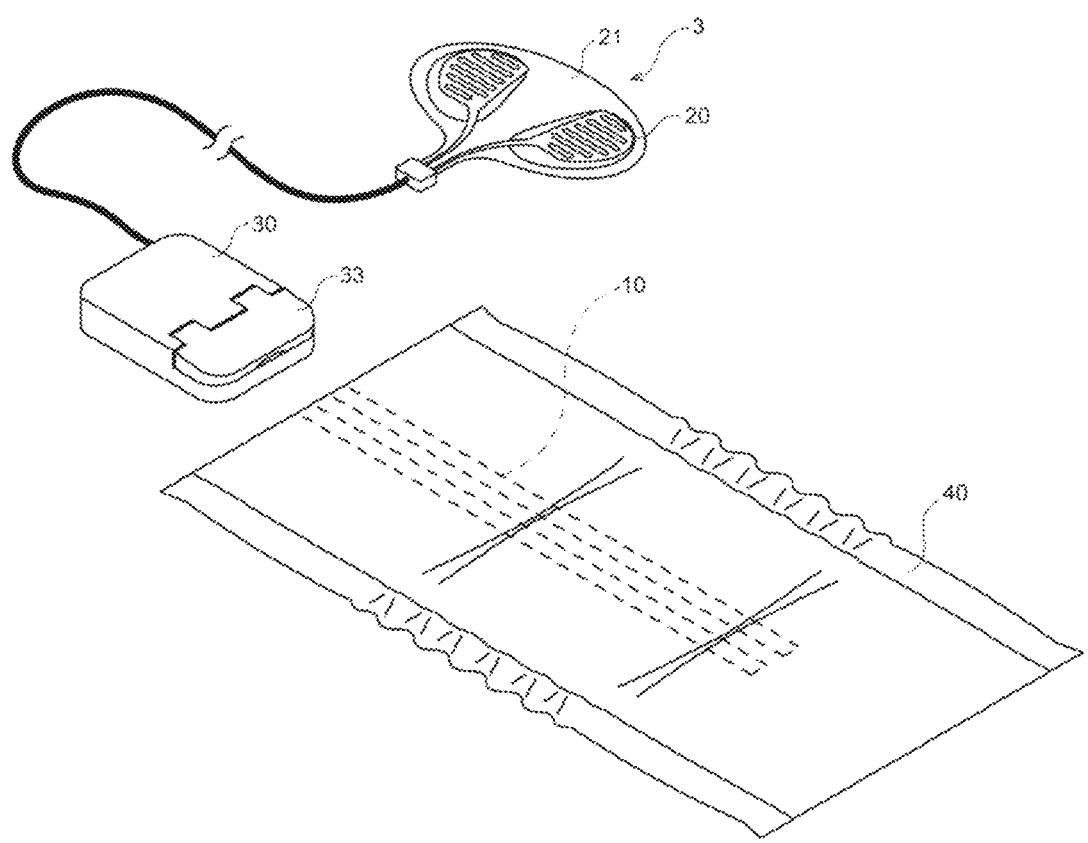
FIG. 5 is an example of an embodiment of the present invention.

A diaper with the sensor 10 for detecting urination as shown in FIG. 5 is also usable as the diaper 40. Examples of such a diaper include the training pad that constitutes the Pisscall nocturnal enuresis training system produced by Awaji-Tec Co., Ltd.

In this case, a urinary incontinence treatment device 3, which is attachable to the diaper 40, includes stimulation pads 20 configured to impart a stimulus to a wearer, and a mechanical member 30. The mechanical member 30 includes (i) a stimulus generation unit 31 for generating a signal for causing the stimulation pads 20 to impart a stimulus to the wearer, (ii) a sensor element connecting part 33 for connecting the sensor 10 to the mechanical member 30, and (iii) a control unit 32 connected to the sensor element connecting part 33 and for causing the stimulus generation unit 31 to generate the signal in response to urination detection by the sensor 10. Attaching the mechanical member 30 (reusable) to the disposable diaper 40 with the sensor 10 easily makes daily use of the device 3 of the invention possible.

The sensor 10 shown in FIG. 5 includes a pair of strip-shaped conductors, and one end of the conductors reaches an end of the diaper 40. The electrical characteristics are different between when urine (water) is absent and when urine (water) is present in the area between the conductors, and based on this difference, the sensor 10 can detect urination. The sensor element connecting part 33 has a clip-like shape, and can hold one end of the conductors together with the diaper 40. In this manner, the sensor element connecting part 33 connects the sensor 10 to the mechanical member 30. The stimulation pads 20 and the mechanical member 30 may be connected via a cable or the like as shown in FIG. 5, or may be connected wirelessly.

The device 3 preferably further includes a waterproof member 21 for protecting the stimulation pads 20 from the urination. This can prevent the wearer from being involved in an electric shock accident when the stimulation pads 20 generate a signal. In this embodiment, the waterproof member 21 has a sheet-like shape covering the entire stimulation pads 20.

Figure 6:
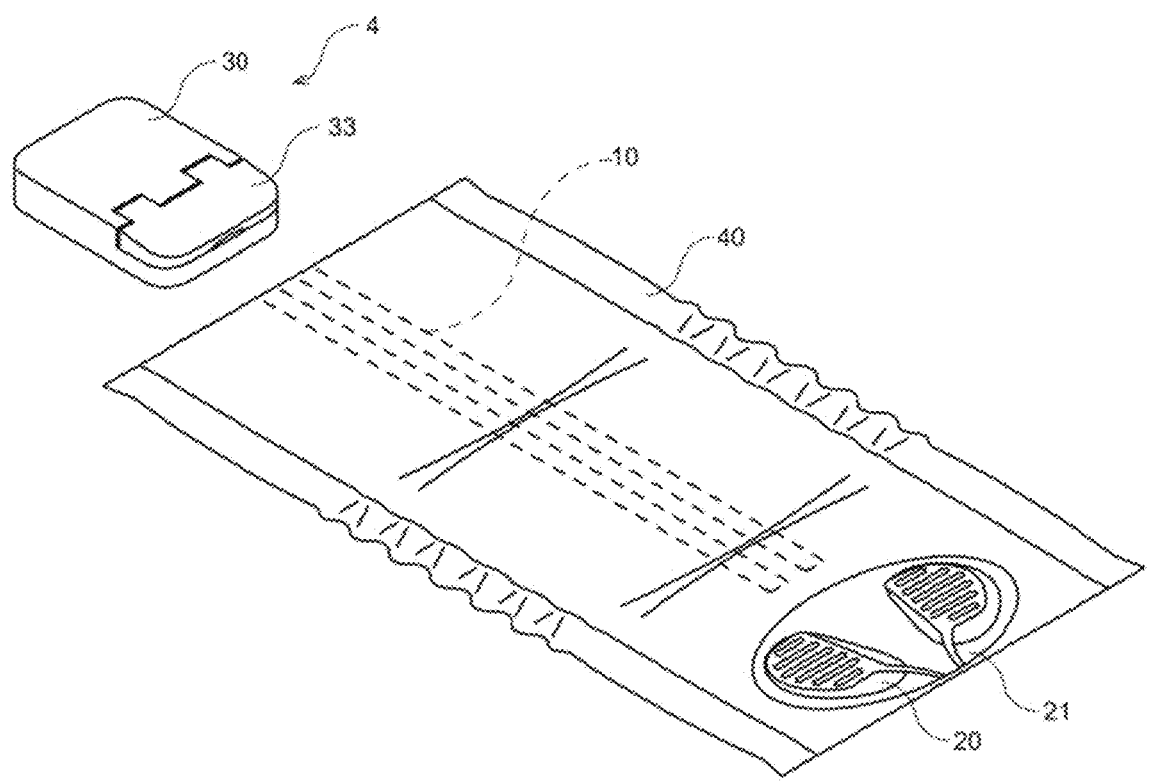
FIG. 6 is an example of an embodiment of the present invention.

Further, a diaper with a sensor 10 for detecting urination and stimulation pads 20 configured to impart a stimulus to a wearer as shown in FIG. 6 can also be used as the diaper 40.

In this case, a urinary incontinence treatment device 4 attachable to the diaper 40 includes a mechanical member 30. The mechanical member 30 includes (i) a stimulus generation unit 31 for generating a signal for causing the stimulation pads 20 to impart a stimulus to the wearer, (ii) a sensor element connecting part 33 for connecting the sensor 10 to the mechanical member 30, and (iii) a control unit 32 connected to the sensor element connecting part 33 and for causing the stimulus generation unit 31 to generate the signal in response to urination detection by the sensor 10.

In FIG. 6, the stimulation pads 20 and the mechanical member 30 are connected wirelessly; however, the connection may be made via a cable or the like as shown in FIG. 5.

EXAMPLES

Example 1

FIG. 4 shows an example of an embodiment of the present invention.

A urinary incontinence treatment device 2 is a diaper, and its mechanical main unit (the mechanical member 30) is positioned at the abdomen. A sensor unit (the sensor 10) is positioned where urine exits, and low-frequency stimulation units (the stimulation pads 20) are positioned at the sacrum area.

The mechanical member 30 and the sensor 10, and the mechanical member 30 and the stimulation pads 20, are respectively connected via electrical wiring (not shown).

Such integral formation prevents displacement due to body movements during sleep.

More specifically, the device was produced in such a manner as to unite a commercially available device used for alarm treatment with a commercially available device used for neuromodulation (low-frequency treatment).

Figure 7:
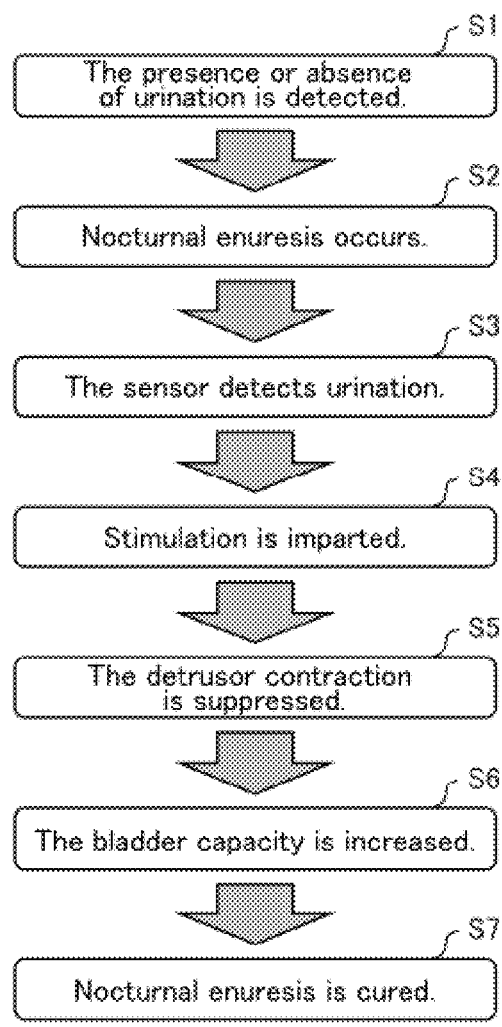
FIG. 7 is a flow chart of an outline of the treatment using the device of the present invention (the mechanism of nocturnal enuresis detection low-frequency treatment).

In the device 2, when the sensor 10 detects urination, the neuromodulation set at the sacrum area is operated, rather than an alarm sound being emitted. In this manner, the bladder is stimulated by neuromodulation (low-frequency treatment) in the occurrence of nocturnal enuresis (urination), rather than the patient being stimulated by an alarm sound and by being woken up by the mother. This can increase bladder capacity to a degree equal to or greater than that achieved in alarm therapy. FIG. 7 shows an outline of this.

As shown in FIG. 7, the method for treating urinary incontinence according to one embodiment of the present invention comprises step S1, in which a sensor detects the presence or absence of urination. When the wearer urinates during the night (step S2), and the sensor detects urination (step S3), the stimulation pads impart a stimulus to the wearer (step S4). The stimulus is preferably imparted to afferent pathways in the sacral spinal cord region. The stimulus suppresses detrusor contraction (step S5), and bladder capacity is increased (step S6). Nocturnal enuresis is accordingly cured within a short period of time (step S7).

Example 2

A test example was performed using a device similar to that of the device 2 of the present invention.
Target
Subject: 8-year old girl
Chief Complaint: Nocturnal Enuresis Every Night The subject was subjected to desmopressin therapy from January 2016, which showed no effects, and thus then visited the Department of Urology, Kyoto Prefectural Medical School.

At the time of the initiation of the treatment, the bladder capacity in the occurrence of nocturnal enuresis was measured to be about 90 to 110 ml. The nocturnal bladder capacity in the occurrence of nocturnal enuresis was calculated from the weights of the diaper before and after the occurrence of nocturnal urination, according to a standard method. After nocturnal enuresis was cured, nocturnal bladder capacity was considered to be the amount of urine immediately after waking up.

The patient had no symptoms other than nocturnal enuresis and had no previous illness.
Method The subject was made to sleep after setting of an alarm for alarm treatment (Chicchi Call produced by Ishiguro Medical System Co., Ltd.) and electrodes for low-frequency treatment device (Uromaster, produced by Medix Japan Co., Ltd.).

A switch was set to on to operate low-frequency treatment without imparting any stimulus by the mother waking up the child immediately when an alarm was emitted in response to nocturnal enuresis detection (while the child continued to sleep). The frequency was 20 Hz, the output current was 10 mA, and the output voltage was 45 V. The stimulus was applied for 10 minutes.
Results After this method was continued for three weeks, nocturnal enuresis occurred only twice a week, and bladder capacity during sleep was confirmed to be increased to 250 ml.

Moreover, daytime bladder capacity (functional bladder capacity) was increased from 270 to 350 ml.

For bladder capacity during sleep, the amount of urine immediately after waking up in the morning without nocturnal enuresis was measured. For daytime bladder capacity (functional bladder capacity), the amount of urine at the patient's limit during daytime was measured.

The above results demonstrate that a combined use of the alarm treatment and electrical stimulation treatment achieved an increase in the bladder capacity during sleep, as well as while awake during daytime.

Example 3

As in Example 2, a 10-year old boy (patient B) and 9-year old girl (patient C) both with nocturnal enuresis were subjected to a test example with a device similar to the device 2 of the present invention.

The results are shown in the following table, together with the results of Example 2 (patient A).

TABLE 1

| Patient | Gender | Age | Nocturnal bladder capacity before experiment | Nocturnal bladder capacity after experiment | Increase percentage (%) | Treatment period (weeks) |
| --- | --- | --- | --- | --- | --- | --- |
| A | Female | 8 | 100 | 250 | 250 | 4 |
| B | Male | 10 | 130 | 250 | 190 | 2 |
| C | Female | 9 | 150 | 240 | 160 | 2 |

Discussion

As disclosed in NPL 1, NPL 2, NPL 3, NPL 4, NPL 5, etc., a 130 to 150% increase in nocturnal bladder capacity is expected when each treatment is performed individually. In contrast, according to the method of the present invention, a maximum of 250% (160 to 250%) increase was confirmed in nocturnal bladder capacity, which is an increase twice as large as that achieved by each treatment performed individually.

The conventional method requires about 6 months for the treatment of nocturnal enuresis. However, according to the method of the present invention, a treatment duration of 2 to 4 weeks (at most ⅓ the duration taken to perform the conventional method) achieved a high therapeutic effect.

The results are surprising since such a significant effect is exerted by giving a stimulus to the nerves involved in suppressing detrusor contraction at the exact time when the detrusor muscle is actually contracting, rather than by simply giving a low-frequency stimulus in any time period of a day.

Although there is no intention to be bound by any theory, it is thought that the effect of suppressing the unrestrained contraction of the bladder wall, the effect of which is an example of the effects of the electrical stimulation treatment, was most significantly achieved by an electrical stimulus imparted at the exact time when the detrusor muscle was contracting. Unrestrained contraction refers to a state in which the bladder wall loses flexibility and becomes unstable, and so the urinary bladder is not capable of being sufficiently filled with urine, causing involuntary urination. That is, the effect of suppressing unrestrained contraction can be referred to as the "effect of stabilizing the bladder wall."

In conventional alarm therapy, the mother, or the like, is required to wake the patient up when the mother hears an alarm sound that is emitted in response to urination detection by the sensor. This is a burden on both the mother and the patient (child). In contrast, according to the mother, the treatment according to the method of the present invention caused no stress on the child since the child was treated during sleep.

Further, since the effect of increasing bladder capacity was confirmed not only at night but also during daytime, the effect can be expected to be exerted on urinary incontinence during daytime.

EXPLANATION OF REFERENCE NUMERALS 1 to 4: Urinary incontinence treatment device
10: Sensor (urine sensor)
20: Stimulation pad (low-frequency stimulation unit, electrode pad)
21: Waterproof member
30: Mechanical member
31: Stimulus generation unit
32: Control unit
33: Sensor element connecting part
40: Diaper

The invention claimed is:

1. A urinary incontinence treatment device including:
   a diaper with a water-absorbent body located at the crotch of a wearer when worn to absorb urine excreted from the wearer and a sensor for electronically detecting urination;
   one or more stimulation pads configured to impart a stimulus to a wearer; and
   a mechanical member including the following:
   (i) a stimulus generation unit for generating a signal for causing the stimulation pads to impart the stimulus to the wearer, and
   (ii) a control unit for causing the stimulus generation unit to generate the signal in response to urination detection by the sensor,
   the mechanical member being attachable to the diaper,
   the stimulation pads being covered by a waterproof member and configured to be attachable to positions at the back of the diaper that correspond to left and right sides of the sacrum of the wearer.

2. The device according to claim 1, wherein the mechanical member is configured to be positioned at the abdomen.

3. The device according to claim 1, wherein the stimulus generation unit supplies an electrical signal to the stimulation pads, and wherein the stimulation pads are electrode pads configured to impart an electrical stimulus to the wearer in response to the supply of the electrical signal.

4. The device according to claim 3, wherein the electrical signal has a frequency of 10 to 50 Hz, and the electrode pads have an output current of 5 to 30 mA and an output voltage of 5 to 60 V.

5. The device according to claim 1, which is for children.

6. The device according to claim 1, which is for adults.

* * * * *